(12) United States Patent
Dai et al.

(10) Patent No.: US 11,617,587 B2
(45) Date of Patent: Apr. 4, 2023

(54) CLAMP

(71) Applicant: SHANGHAI HANYU MEDICAL TECHNOLOGY CO., LTD., Shanghai (CN)

(72) Inventors: Yufeng Dai, Shanghai (CN); Bingyue Pan, Shanghai (CN); Zhijie Wang, Shanghai (CN)

(73) Assignee: SHANGHAI HANYU MEDICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 17/597,570

(22) PCT Filed: Apr. 26, 2021

(86) PCT No.: PCT/CN2021/089767
§ 371 (c)(1),
(2) Date: Jan. 12, 2022

(87) PCT Pub. No.: WO2022/068188
PCT Pub. Date: Apr. 7, 2022

(65) Prior Publication Data
US 2022/0314046 A1     Oct. 6, 2022

(30) Foreign Application Priority Data

Sep. 29, 2020 (CN) .......................... 202011051160.0
Sep. 29, 2020 (CN) .......................... 202022194917.3
(Continued)

(51) Int. Cl.
*A61B 17/122* (2006.01)
*A61B 17/00* (2006.01)

(52) U.S. Cl.
CPC .. *A61B 17/122* (2013.01); *A61B 2017/00243* (2013.01); *A61B 2017/00867* (2013.01)

(58) Field of Classification Search
CPC ...... A61F 2/2403; A61F 2/2442; A61F 2/246; A61B 17/122; A61B 2017/00243; A61B 2017/00867
See application file for complete search history.

(56) References Cited

U.S. PATENT DOCUMENTS 7,563,267 B2 * 7/2009 Goldfarb ............ A61B 17/0469
606/151
7,635,329 B2 * 12/2009 Goldfarb ................ A61B 17/29
600/37

(Continued)

FOREIGN PATENT DOCUMENTS

CN    109715111 A    5/2019
CN    110290764 A    9/2019
(Continued)

*Primary Examiner* — Ryan J. Severson
(74) *Attorney, Agent, or Firm* — Bayramoglu Law Offices LLC

(57) ABSTRACT

A clamp includes upper clamp assemblies, lower clamp assemblies, a base, a locking unit, a connecting rod arm, expandable arms and a central occluding woven net. The upper clamp assemblies and the lower clamp assemblies are quantitatively identical and cooperate in opening and closing to form a clamping portion. The clamp can effectively occlude the regurgitation on two sides of the clamp through the expandable arms on the two sides. By means of the central occluding woven net, the clamp can further reduce the central regurgitation, decrease the stress on the leaflet and prevent the damage to the leaflet; and the clamp firmly closes the lower clamp assemblies in a mechanical locking manner, such that the clamp does not drop easily after implanted into the body. The clamp can be implanted through the femoral vein puncture and transseptal puncture (TSP) with minimal invasion, to repair the mitral valve.

20 Claims, 8 Drawing Sheets

(30) Foreign Application Priority Data

Jan. 14, 2021 (CN) .......................... 202110049494.2
Jan. 14, 2021 (CN) .......................... 202120100082.2

(56) References Cited

U.S. PATENT DOCUMENTS

| | | | | |
|---|---|---|---|---|
| 8,052,592 | B2* | 11/2011 | Goldfarb | A61F 2/246 600/37 |
| 8,216,256 | B2* | 7/2012 | Raschdorf, Jr. | A61B 17/10 606/151 |
| 8,465,540 | B2* | 6/2013 | Straubinger | A61F 2/07 623/1.24 |
| 8,945,177 | B2* | 2/2015 | Dell | A61F 2/2466 606/151 |
| 9,011,468 | B2* | 4/2015 | Ketai | A61F 2/246 606/198 |
| 9,510,829 | B2* | 12/2016 | Goldfarb | A61B 17/04 |
| 9,572,666 | B2* | 2/2017 | Basude | A61F 2/2463 |
| 10,076,415 | B1* | 9/2018 | Metchik | A61F 2/246 |
| 10,159,570 | B1* | 12/2018 | Metchik | A61F 2/2466 |
| 10,188,392 | B2* | 1/2019 | Wei | A61F 2/246 |
| 10,231,837 | B1* | 3/2019 | Metchik | A61F 2/246 |
| 10,524,912 | B2* | 1/2020 | Wei | A61B 17/1227 |
| 10,548,614 | B2* | 2/2020 | Hernández | A61B 17/00234 |
| 10,898,327 | B2* | 1/2021 | Dixon | A61F 2/2466 |
| 10,952,853 | B2* | 3/2021 | Delgado | A61L 27/04 |
| 10,959,846 | B2* | 3/2021 | Marr | A61B 17/1227 |
| 11,065,119 | B2* | 7/2021 | Abunassar | A61B 17/08 |
| 11,185,413 | B2* | 11/2021 | Basude | A61F 2/2463 |
| 11,304,715 | B2* | 4/2022 | Goldfarb | A61F 2/246 |
| 2003/0120341 | A1* | 6/2003 | Shennib | A61B 5/0215 623/2.12 |
| 2004/0049207 | A1* | 3/2004 | Goldfarb | A61B 50/30 606/139 |
| 2007/0197858 | A1* | 8/2007 | Goldfarb | A61B 17/0401 600/37 |
| 2009/0163934 | A1* | 6/2009 | Raschdorf, Jr. | A61B 17/00234 606/139 |
| 2010/0022823 | A1* | 1/2010 | Goldfarb | A61B 17/0401 600/37 |
| 2011/0208290 | A1 | 8/2011 | Straubinger et al. | |
| 2013/0066341 | A1* | 3/2013 | Ketai | A61F 2/2454 606/151 |
| 2013/0066342 | A1* | 3/2013 | Dell | A61F 2/2466 606/151 |
| 2014/0236198 | A1* | 8/2014 | Goldfarb | A61B 17/0469 606/151 |
| 2015/0257883 | A1* | 9/2015 | Basude | A61B 17/0682 623/2.11 |
| 2016/0174979 | A1* | 6/2016 | Wei | A61F 2/246 606/151 |
| 2016/0287387 | A1* | 10/2016 | Wei | A61F 2/2454 |
| 2018/0146966 | A1* | 5/2018 | Hernández | A61B 17/1227 |
| 2018/0296334 | A1* | 10/2018 | Dixon | A61F 2/2403 |
| 2018/0325661 | A1* | 11/2018 | Delgado | A61B 17/1285 |
| 2018/0325671 | A1* | 11/2018 | Abunassar | A61B 17/08 |
| 2019/0000613 | A1* | 1/2019 | Delgado | A61B 17/00 |
| 2019/0142589 | A1* | 5/2019 | Basude | A61F 2/2463 623/2.11 |
| 2020/0323549 | A1* | 10/2020 | Goldfarb | A61F 2/246 |
| 2022/0240920 | A1* | 8/2022 | Goldfarb | A61B 17/08 |

FOREIGN PATENT DOCUMENTS

| | | |
|---|---|---|
| CN | 111317596 A | 6/2020 |
| CN | 111449805 A | 7/2020 |
| CN | 211325891 U | 8/2020 |
| CN | 211485094 U | 9/2020 |
| CN | 112120831 A | 12/2020 |

* cited by examiner

CLAMP

CROSS REFERENCE TO THE RELATED APPLICATIONS

This application is the national phase entry of International Application No. PCT/CN2021/089767, filed on Apr. 26, 2021, which is based upon and claims priority to Chinese Patent Applications No. 202011051160.0, filed on Sep. 29, 2020; No. 202022194917.3, filed on Sep. 29, 2020; No. 202110049494.2, filed on Jan. 14, 2021; and No. 202120100082.2, filed on Jan. 14, 2021; the entire contents of which are incorporated herein by reference.

TECHNICAL FIELD

The present invention relates to the field of medical appliances, particularly to a repair system for treating mitral valve regurgitation, and specifically to a clamp having an expandable arm and an occluding woven net.

BACKGROUND

The mitral valve, known as the left atrioventricular valve, is attached to the left atrioventricular fibrous ring. The function of the mitral valve depends on the structural integrity. The mitral valve is normally composed of valve rings, valve leaflets, chordae tendineae and papillary muscles. The mitral valve is functionally integral, provided that the valve rings have the appropriate size, the valve leaflets are structurally integral, the papillary muscles in contraction pull the chordae tendineae to achieve support effects of the valve leaflets, the left ventricular muscles in contraction generate an appropriate closure force and the ventricles are morphologically and functionally normal. The above factors jointly dominate the integrity of the mitral valve; and any abnormal factor will lead to mitral regurgitation (MR), which is the most common type of heart valve disease.

With the scientific and technological advancements, several interventional devices for treating the MR have been developed by the medical appliance manufacturers in China and other countries in recent years. There mainly have been the edge-to-edge repair, annuloplasty, and chordae tendineae implantation, etc. Presently, the edge-to-edge repair, typified by the Abbott MitraClip and the Edwards PASCAL, is superior to other technologies for its long history and better safety. The MitraClip is implemented by making the transcatheter femoral vein puncture, routing the clip through transseptal puncture (TSP) downward from the atrium to the periphery of the mitral valve, fixing free edges of anterior and anterior leaflets, and clamping the mitral valve into two orifices with the clip for desirable alignment of the leaflets and less regurgitation in end-systole. The Edwards PASCAL can separately capture the leaflets, though it also makes the femoral vein puncture and the transcatheter TSP and clamps the mitral valve into the two orifices with the clip.

However, due to a limited range of the clip and a wide regurgitation range for the mitral valve of the patient, the edge-to-edge repair proposed in the MitraClip and the Chinese Patent CN 211325891 U still has the regurgitation or leakage problem on two sides and top of the clip after the mitral valve is clamped by the clip, and the stresses on the leaflets are large. As a result, the desirable effect cannot be achieved until multiple clips are clinically used, thus increasing the probability of valvular stenosis upon repair of the mitral valve, making the procedure more difficult and riskier and further increasing the medical expenses. The PASCAL can occlude the two sides, center and top of the clamp to prevent the regurgitation. However, the closure force of the self-locking clamp for the elastic lower clamp assemblies is changeable and not firm enough, such that the clamp drops easily when implanted into the body.

Compared with the prior art, the present invention has the following advantages. The valve clamp can effectively occlude the regurgitation on two sides of the clamp through the expandable arms on the two sides. By means of the central occluding woven net, the valve clamp can further reduce the central regurgitation, decrease the stress on the leaflet and prevent the damage to the leaflet. The valve clamp firmly closes the lower clamp assemblies in a mechanical locking manner, such that the clamp does not drop easily after implanted into the body. The clamp can be implanted through the femoral vein puncture and TSP with minimal invasion, to repair the mitral valve. The device can implement the procedure without stopping the heartbeat and form an effective double-orifice structure. Furthermore, the device shortens the time of the procedure, reduces the injury degree, and reduces the difficulty and risk of the procedure.

SUMMARY

An objective of the present invention is to provide a clamp having an expandable arm and an occluding woven net, to overcome the shortages of the prior art. The present invention can solve the problem that the existing clamp cannot occlude two sides, center and top of the clamp at the same time to prevent regurgitation, and achieve firm locking.

A clamp includes upper clamp assemblies, lower clamp assemblies, a base, a locking unit and expandable arms, where the upper clamp assemblies and the lower clamp assemblies are quantitatively identical and cooperate in opening and closing to form a clamping portion; the base includes a base body and a base support rod, and the base support rod is perpendicularly provided on an upper surface of the base body; the locking unit is movably sleeved on the base support rod, and the bottom of the locking unit abuts against and is supported on the upper surface of the base body; a lower portion of each of the upper clamp assemblies is fixedly provided on a side of the locking unit, and the lower clamp assemblies are movably connected to the locking unit and located below the upper clamp assemblies; each of the expandable arms is detachably provided on an upper portion of each of the lower clamp assemblies and extends toward two sides of a clamping bottom plate of each of the lower clamp assemblies, respectively; when the upper clamp assemblies and the lower clamp assemblies are in a working clamped state, an outer expansion edge of each of the expandable arms is located between two adjacent or opposite lower clamp assemblies to clamp valves on two sides of the clamping portion, thereby expanding a clamping range; and the expandable arms are deformable and are in a contracted state in delivery, such that the clamp is compressed overall into a delivery system to reduce an injury in a procedure.

Preferably, each of the upper clamp assemblies may include elastic upper clamping plates having a shape memory function; at least one threading hole may be formed in a plate body of each of the elastic upper clamping plates; a side, facing toward each of the lower clamp assemblies, of each of the elastic upper clamping plates may be provided with a rough structure; and the rough structure may include a toothed structure, a barbed structure or a protrusive structure.

Preferably, the upper clamp assemblies each may further include an upper clamp connecting bottom plate, two ends of the upper clamp connecting bottom plate may be respectively provided with the elastic upper clamping plates, the upper clamp connecting bottom plate and the elastic upper clamping plates at the two ends of the upper clamp connecting bottom plate may be integrally formed into a concave structure, an upper clamp through hole may be formed in a middle of the upper clamp connecting bottom plate, an upper clamp guiding limit hole may be formed in a lower portion of each of the two elastic upper clamping plates in a penetrating manner, and the upper clamp guiding limit hole may be configured to release the stress in an upper clamp heat treatment forming process; and an upper surface of the upper clamp connecting bottom plate may be attached to an underside of the locking unit, and an inner side of the lower portion of each of the two elastic upper clamping plates may be attached to an outer side of the locking unit.

Preferably, each of the elastic upper clamping plates having the shape memory function may have a preset expansion angle α, and α=30-135°.

Preferably, each of the lower clamp assemblies may include a lower clamp bottom plate and lower clamp side plates perpendicularly provided on two sides of the lower clamp bottom plate, the lower clamp bottom plate and the lower clamp side plates may be formed into an accommodation cavity cooperating with each of the upper clamp assemblies; and a lower portion of each of the lower clamp side plates may be connected to an outward expansion plate and a hinge plate, and movably connected to the locking unit through the hinge plate expanding outward.

Preferably, a hinge hole for connecting each of the lower clamp assemblies to the locking unit may be formed in the hinge plate in a penetrating manner; and a linkage hole may be formed in the outward expansion plate.

Preferably, an inner side of an upper edge of each of the lower clamp bottom plate and the lower clamp side plates is rounded or is provided with a turnup extending outward in an arc.

Preferably, the locking unit may include a locking base, a hollow locking accommodation cavity may be formed in a lower portion of the locking base, an oblique lug boss protruding toward the cavity may be provided on a sidewall of the locking accommodation cavity, and the oblique lug boss may be configured to be embedded into the base support rod to locate the locking unit on the base. The locking unit may use a mechanical locking manner; and when the lower clamp assemblies are closed, the locking unit may be turned off and clasp the base support rod, thereby limiting opening of each of the expandable arms.

Preferably, each of the expandable arms may include a strip-shaped or tubular outer expansion frame, and each of the expandable arms may be of any shape including but not limited to a semicircular shape, an ω shape formed by connecting two semi-rings, a semicircular shape formed by docking two irregular curves, a docked trapezoidal shape, or a U shape.

Preferably, an inner expansion woven net may be provided at a concave place of the outer expansion frame of each of the expandable arms.

Preferably, a pore size of the inner expansion woven net of each of the expandable arms may be less than an outer diameter of a regurgitation body.

Preferably, each of the upper clamp assemblies may include two elastic upper clamping plates oppositely arranged on two sides of the locking unit; and correspondingly, two lower clamp assemblies may be provided.

Preferably, the expandable arms may be respectively connected to the lower clamp assemblies in a manner including but not limited to a spliced connection, a riveted connection, a welded connection or a threaded connection; and the expandable arms may be made of an alloy having the shape memory function or a degradable polymer material.

Preferably, the alloy may include but not limited to a nitinol and a magnesium alloy having the shape memory function, and the polymer material may include a degradable poly-L-lactic acid.

Preferably, the rough structure may be toothed rows or barbed rows obliquely formed from two sides of a plate body of each of the elastic upper clamping plates, or an integral toothed row structure continuously formed by the two sides of the plate body of each of the elastic upper clamping plates.

Preferably, the clamp may further include a connecting rod arm, and the connecting rod arm may include a connecting rod bottom plate and connecting rod side plates perpendicular to a side of the connecting rod bottom plate; a lower portion of each of the connecting rod side plates may be movably connected to the base body of the base, and an upper portion of each of the connecting rod side plates may be movably connected to a linkage hole of each of the lower clamp assemblies, thereby forming a four-rod linkage unit; and an accommodation groove formed by the connecting rod bottom plate and the connecting rod side plates may be matched with an external contour of the lower portion of each of the lower clamp assemblies.

Preferably, the clamp may include an occluding woven net; the occluding woven net may be located in a center of an upper portion of the clamp, and provided on the locking unit; and the occluding woven net may be linked with the expandable arms to change from a contracted state to an expanded state, thereby reducing central regurgitation, decreasing the stress on a leaflet, and preventing the damages to the leaflet.

Preferably, the occluding woven net in the expanded state may be of a hazelnut shape, an ellipsoidal shape, a conical shape, an ingot shape, a pillow shape, a trumpet shape, a saddle shape, a spherical shape, an oblate spheroid shape or an irregular shape; a preserved hole for conveniently cooperating with the delivery system may be formed in a top of the occluding woven net; and a bottom of the occluding woven net may be connected to a periphery of the locking unit through end portions of the net, or connected to a top of the locking unit through a bottom contracting end of the occluding woven net.

Preferably, a biocompatible polyethylene terephthalate (PET) film may be coated on an outer surface of each of the upper clamp assemblies, the lower clamp assemblies, the base, the locking unit, the expandable arms, the connecting rod arm and the occluding woven net.

Compared with the prior art, the present invention has the following advantages. The valve clamp can effectively occlude the regurgitation on two sides of the clamp through the expandable arms on the two sides. By means of the central occluding woven net, the clamp can further reduce the central regurgitation, decrease the stress on the leaflet and prevent the damage to the leaflet. The clamp can be implanted through the femoral vein puncture and TSP with minimal invasion, to repair the mitral valve. The device can implement the procedure without stopping the heartbeat and form an effective double-orifice structure. Furthermore, the device shortens the time of the procedure, reduces the injury degree, and reduces the difficulty and risk of the procedure.

DETAILED DESCRIPTION OF THE EMBODIMENTS

Figure 1:
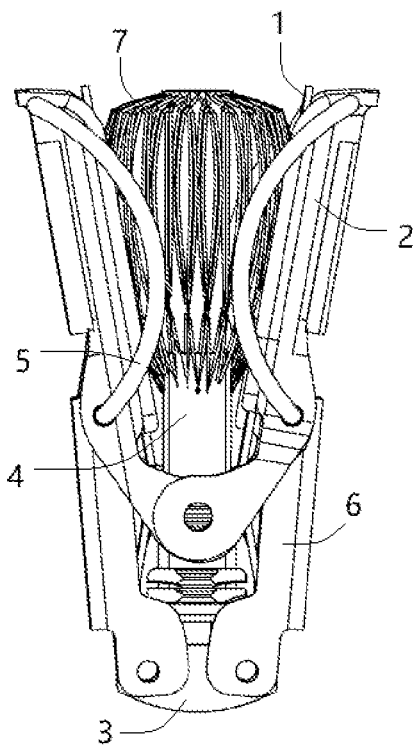
FIG. 1 is a schematic structural view of a clamp having an expandable arm and an occluding woven net according to the present invention.
Figure 2:
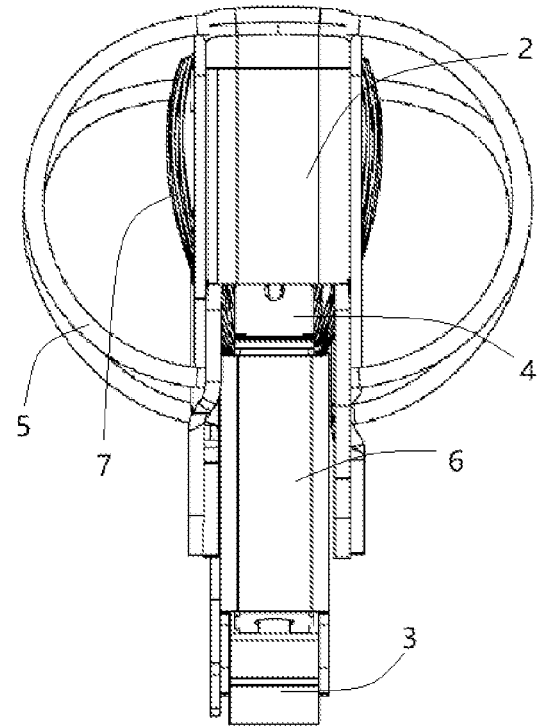
FIG. 2 is a side view of a clamp.
Figure 3:
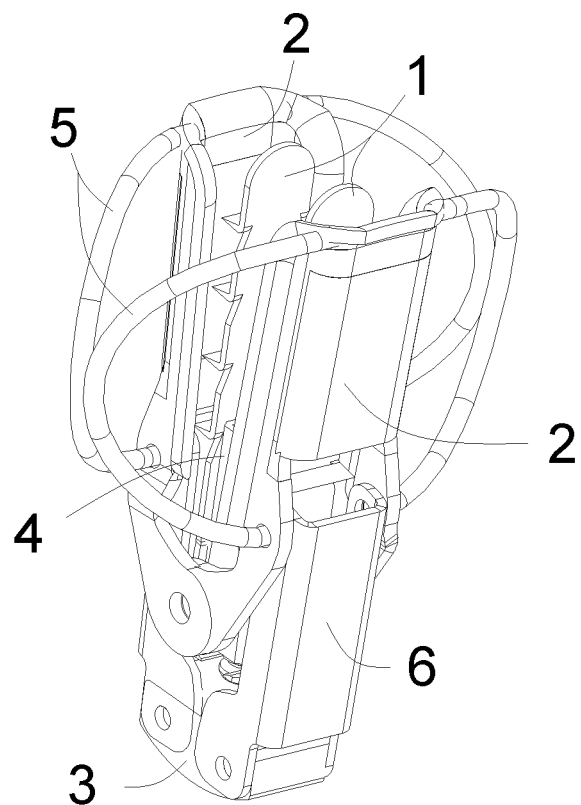
FIG. 3 is a partially structural view of a clamp without an occluding woven net according to the present invention.
Figure 4:
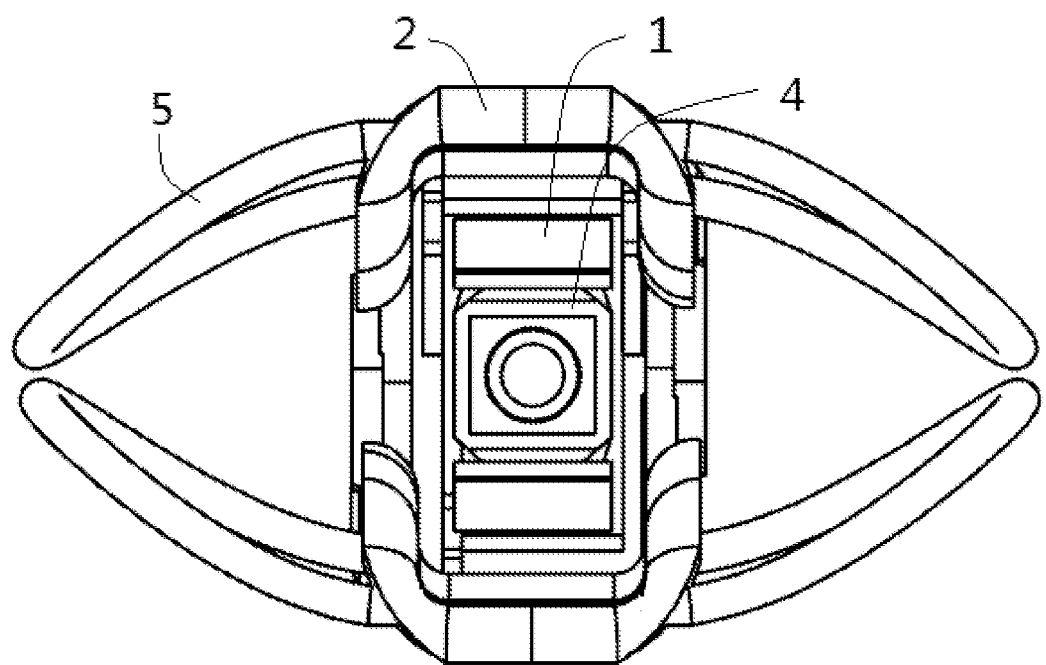
FIG. 4 is a top view of a clamp without an occluding woven net in an original state.
Figure 5:
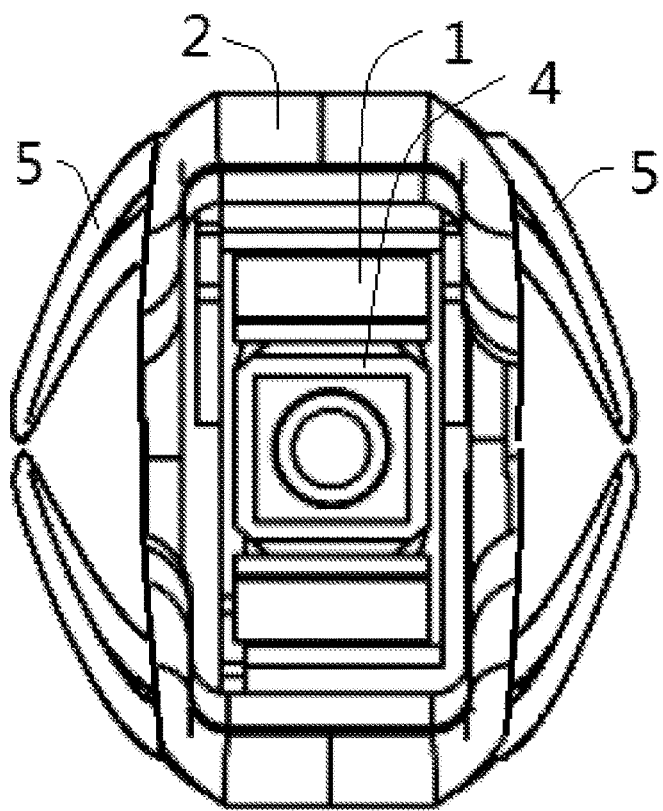
FIG. 5 is a top view of a clamp without an occluding woven net in a compressed state.

To make the objectives, technical solutions and advantages of the embodiments of the present invention clearer, the following clearly and completely describes the technical solutions in the embodiments of the present invention with reference to accompanying drawings in the embodiments of the present invention. Apparently, the described embodiments are some rather than all the embodiments of the present invention. All other embodiments obtained by those of ordinary skill in the art based on the embodiments of the present invention without making inventive efforts shall fall within the scope of protection of the present invention.

Terms "system", "device", "unit" and/or "module" herein are used as a method to distinguish different components, elements, parts, sections or assemblies of different levels. However, the terms may be displaced by other expressions if they may achieve the same purpose.

As used in the specification and claims, the singular forms "a", "an", "one" and/or "the" may be intended to include the plural forms as well, unless the context clearly indicates otherwise. Generally, the terms "include" and "comprise" only indicate that explicitly marked steps and elements are included; these steps and elements do not form any exclusive enumeration; and the method or the device may also include other steps or elements.

The flow chart used here is merely for illustrating operations executed by the system according to the embodiment of the present invention. The front or rear operations are not accurately executed according to an order. Reversely, these steps may be executed in an inverted order or at the same time. Furthermore, other operations may also be added to these steps, or one or more operations may also be removed from these steps.

Referring to FIG. 1 to FIG. 12D, a clamp having an expandable arm and an occluding woven net includes upper clamp assemblies 1, lower clamp assemblies 2, a base 3, a locking unit 4, expandable arms 5, connecting rod arms 6 and an occluding woven net 7. After implanted into the human body through a minimally invasive procedure, the clamp for the heart valve prosthesis can be used to effectively treat the MR and the tricuspid regurgitation (TR).

The upper clamp assemblies 1 and the lower clamp assemblies 2 are quantitatively identical and cooperate in opening and closing to form a clamping portion. Preferably, there are two upper clamp assemblies 1 and two lower clamp assemblies 2 that are symmetrically and movably connected to two sides of the locking unit 4. Certainly, there may also be multiple upper clamp assemblies and lower clamp assemblies according to an actual need.

The lower clamp assemblies 2, the base 3, the locking unit 4 and the connecting rod arms 6 are formed into a four-rod unit, making the valve clamp opened and closed more easily.

The base 3 includes a base body 31 and a base support rod 32, and the base support rod 32 is perpendicularly provided on an upper surface of the base body 31. Two base connecting holes 33 are formed in a side of the base body 31, and a base threaded hole 34 is formed in an underside of the base 31.

The locking unit 4 is sleeved on the base support rod 32 and includes a bottom supported on the upper surface of the base body 31; a lower portion of each of the upper clamp assemblies 1 is fixedly provided on a side of the locking unit 4, and the lower clamp assemblies 2 are movably connected to the locking unit 4 and located below the upper clamp assemblies 1, respectively. The locking unit 4 uses a mechanical locking manner; and when the lower clamp assemblies 2 are closed, the locking unit 4 is turned off and clasps the base support rod 32, thereby limiting opening of each of the expandable arms 5.

Figure 7:
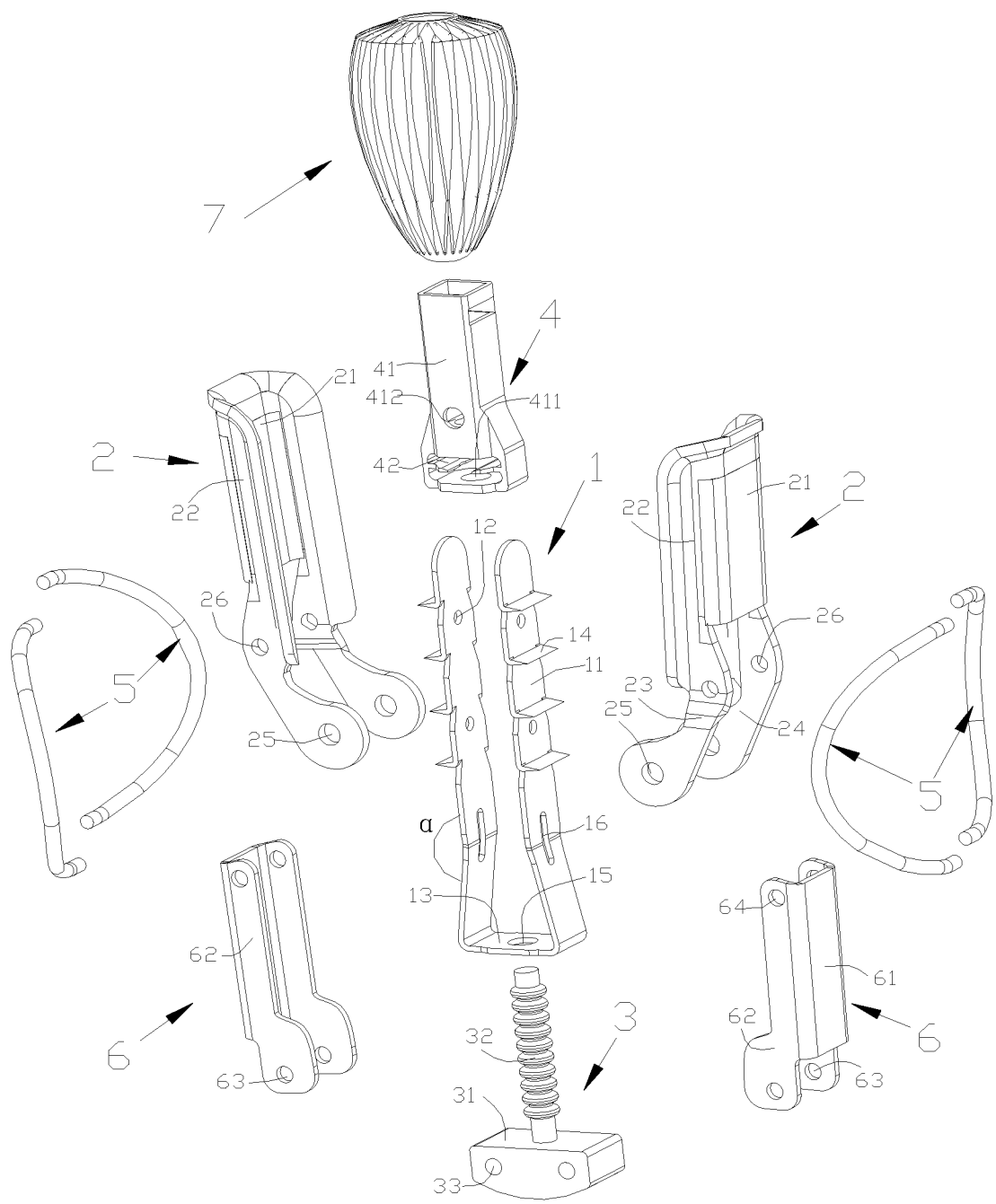
FIG. 7 is a partial breakdown structure of a clamp having a semicircular expandable arm and a hazelnut-shaped occluding woven net according to the present invention.

In different embodiments, the base support rod 32 is a threaded rod or a disc string rod (FIG. 1 and FIG. 7).

Each of the expandable arms 5 is detachably provided on an upper portion of each of the lower clamp assemblies 2 and extends toward two sides of a clamping bottom plate of each of the lower clamp assemblies 2, respectively. When the upper clamp assemblies 1 and the lower clamp assemblies 2 are in a working clamped state, an outer expansion edge of each of the expandable arms 5 is located between two adjacent or opposite lower clamp assemblies 2 to clamp valves on two sides of the clamping portion, thereby expanding a clamping range. The expandable arms 5 are deformable and are in a contracted state in delivery, such that the clamp is overall compressed into a delivery system to reduce an injury in a procedure.

Alternatively, the expandable arms 5 may also be integrally formed on the lower clamp assemblies 2, respectively.

The occluding woven net 7 is in a center of an upper portion of the clamp and provided on the locking unit 4. The occluding woven net 7 is linked with the expandable arms 5 to change from a contracted state to an expanded state, thereby reducing central regurgitation, decreasing the stress on a leaflet and preventing the damage to the leaflet.

Figure 6:
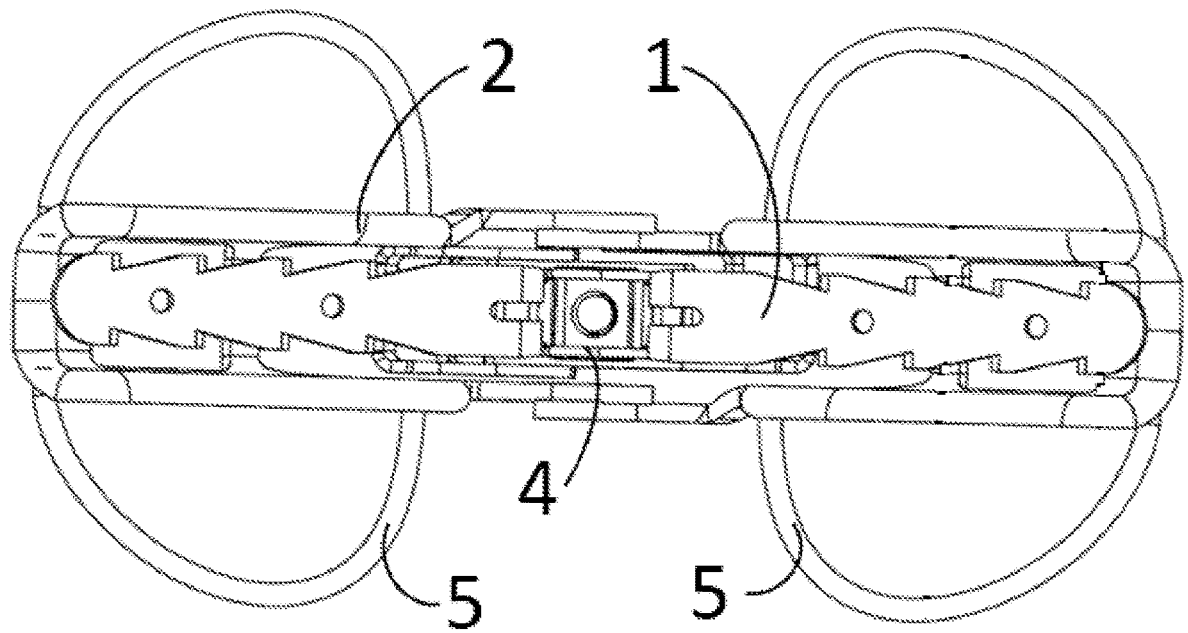
FIG. 6 is a schematic view of an expandable arm for increasing a capture area.
Figure 8A:
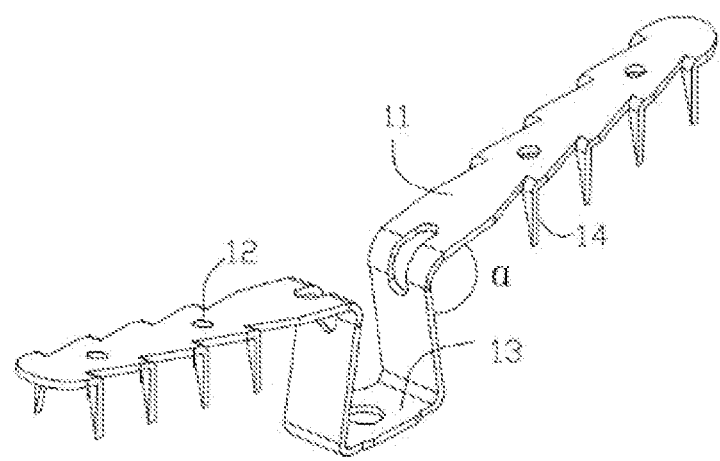
FIGS. 8A-8B are schematic views of an upper clamp assembly opened at nearly 90° according to different embodiments.
Figure 8B:
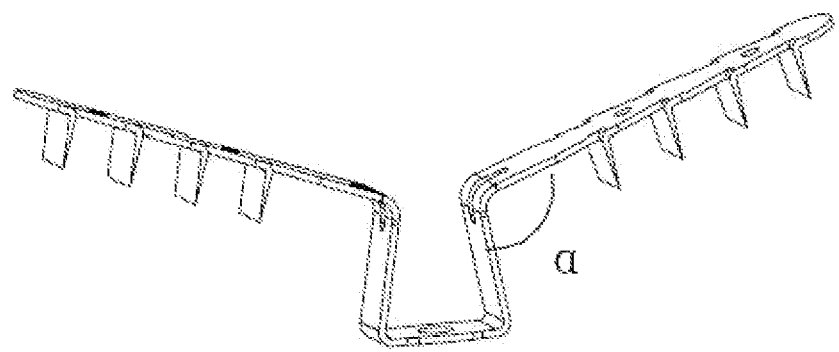
Figure 9:
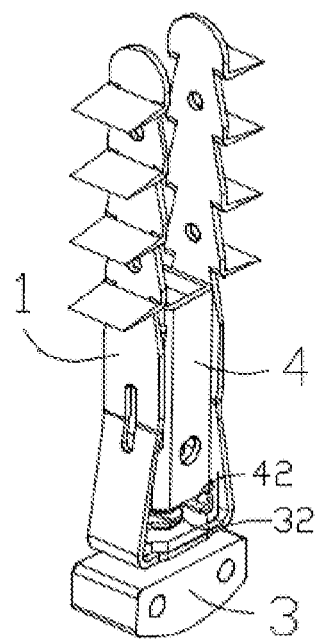
FIG. 9 is a partially structural view of a clamp having an upper clamp assembly according to the present invention.
Figure 10:
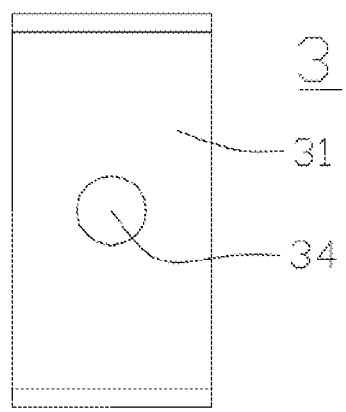
FIG. 10 is a bottom view of a base.

Each of the upper clamp assemblies 1 includes elastic upper clamping plates 11 having a shape memory function; at least one threading hole 12 is formed in a plate body of each of the elastic upper clamping plates 11; a side, facing toward each of the lower clamp assemblies 2, of each of the elastic upper clamping plates 11 is provided with a rough structure 14; and the rough structure includes a toothed structure, a barbed structure or a protrusive structure. The rough structure may be of a structure in which single teeth (FIGS. 3, 7, 8A, 8B and 9) are parallel and may also be of a structure in which double teeth are arranged side by side (FIG. 6 and FIGS. 8A-8B). In an optional example, the rough structure 14 includes multiple uniformly-spaced flat plate-like teeth protruding perpendicularly outward from a back of each of the elastic upper clamping plates 11, and side-by-side rectangular sheets or rectangular teeth protruding outward from an outer side of each of the elastic upper clamping plates 11. The uniformly-spaced manner may also refer that a space from one end to the other end is gradually decreased or increased. The rough structure 14 is toothed rows or barbed rows obliquely formed from two sides of the plate body of each of the elastic upper clamping plates 11, or an integral toothed row structure continuously formed by the two sides of the plate body of each of the elastic upper clamping plates.

In an embodiment, the rough structure 14 is the toothed rows or barbed rows obliquely formed from the two sides of the plate body of each of the elastic upper clamping plates 11. The rough structure 14 functions to improve the clamping force on the target tissue during clamping, and enhance the stability of capturing the leaflet in procedure. The protrusions of the rough structure 14 may be sequentially lengthened, shortened or unchanged from bottom to top, and may also be arranged by spacing a long one or a short one.

The threading hole 12 is configured to thread a pull wire (which is not described herein) for fine tuning and the like in the procedure.

Each of the upper clamp assemblies 1 includes two elastic upper clamping plates 11 oppositely arranged on two sides of the locking unit 4; and correspondingly, two lower clamp assemblies 2 are provided.

Each of the upper clamp assemblies 1 further includes an upper clamp connecting bottom plate 13, two ends of the upper clamp connecting bottom plate 13 are respectively provided with the elastic upper clamping plates 11, the upper clamp connecting bottom plate 13 and the elastic upper clamping plates 11 at the two ends of the upper clamp connecting bottom plate 13 are integrally formed into a concave structure, an upper clamp through hole 15 is formed in a middle of the upper clamp connecting bottom plate 13, an upper clamp guiding limit hole 16 is formed in a lower portion of each of the two elastic upper clamping plates 11 in a penetrating manner, and the upper clamp guiding limit hole 16 is configured to release the stress in an upper clamp heat treatment forming process. An upper surface of the upper clamp connecting bottom plate 13 is attached to an underside of the locking unit 4, and an inner side of the lower portion of each of the two elastic upper clamping plates 11 is attached to an outer side of the locking unit 4.

Further, each of the elastic upper clamping plates 11 having the shape memory function has a preset expansion angle α, and α=30-135°, and preferably 90°.

In work, the elastic upper clamping plates 11 each achieve the expansion angle α through two separate manipulation wires to sequentially and individually capture the leaflet.

Each of the lower clamp assemblies 2 includes a lower clamp bottom plate 21 and lower clamp side plates 22 perpendicularly provided on two sides of the lower clamp bottom plate 21, and the lower clamp bottom plate 21 and the lower clamp side plates 22 are formed into an accommodation cavity cooperating with each of the upper clamp assemblies 1. A lower portion of each of the lower clamp side plates 22 is connected to an outward expansion plate 23 and a hinge plate 24, and movably connected to the locking unit 4 through the hinge plate 24 expanding outward.

Further, an inner side of an upper edge of each of the lower clamp bottom plate 21 and the lower clamp side plates 22 is rounded or is provided with a turnup extending outward in an arc.

A hinge hole 25 for connecting each of the lower clamp assemblies 2 to the locking unit 4 is formed in the hinge plate 24 in a penetrating manner; and a linkage hole 26 is formed in the outward expansion plate 23.

Protrusions of a strip shape and the like may be provided in the accommodation cavity to make the clamping more stable.

The base body 31 of the base 3 may be of a structure such as a hemispheroid, a spherical crown, a bullet shape and a symmetric flat tip.

The locking unit 4 includes a locking base 41, a hollow locking accommodation cavity is formed in a lower portion of the locking base 41, an oblique lug boss 42 protruding toward the cavity is provided on a sidewall of the locking accommodation cavity, and the oblique lug boss 42 is configured to be embedded into the base support rod 32 to locate the locking unit 4 on the base 3. Further, a coupling channel is vertically formed in the locking base 41 in a penetrating manner, and the base support rod 32 of the base 3 is inserted into the coupling channel through a bottom plate hole 411 at the bottom of the locking base 41.

Further, a locking hinge hole 412 is formed in a side, adjacent to the side provided with the upper clamp assemblies 1, of the locking base 41, to movably connect the hinge plate 24 of each of the lower clamp assemblies 2 to the corresponding side of the locking base 41.

When the base support rod 32 is the disc string rod, two oblique lug bosses 42 oppositely flush with each other are provided in the locking accommodation cavity at the lower end of the locking base 41; and the oblique lug bosses may also be plane lug bosses for embedding disc strings on the base support rod 32 to locate the locking unit 4 on the base 3.

The movable connection includes but is not limited to a hinged connection, a pivoted connection, etc.

Each of the expandable arms 5 includes a strip-shaped or tubular outer expansion frame 51, and each of the expandable arms is of any shape (FIGS. 11A-11D) including but not limited to a semicircular shape (FIG. 1-FIG. 7), an 6) shape formed by connecting two semi-rings (FIG. 11C), a semicircular shape formed by docking two irregular curves (FIG. 11A), a docked trapezoidal shape (FIG. 11B), or a U shape (not shown in the figures).

Figure 11A:
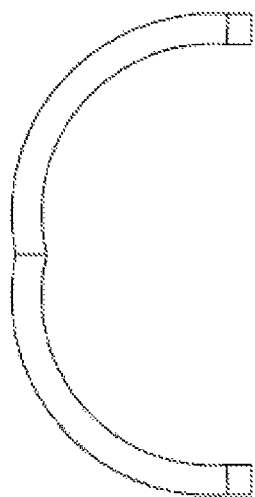
FIGS. 11A-11D are schematic structural view of an expandable arm according to different embodiments.
Figure 11B:
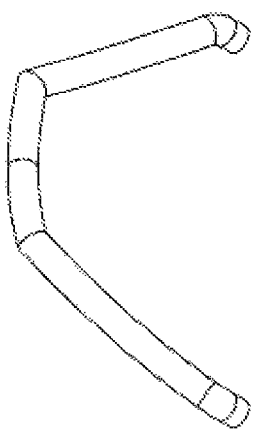
Figure 11C:
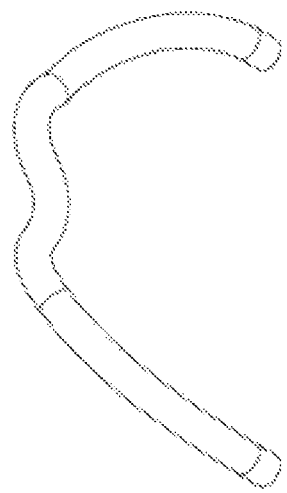
Figure 11D:
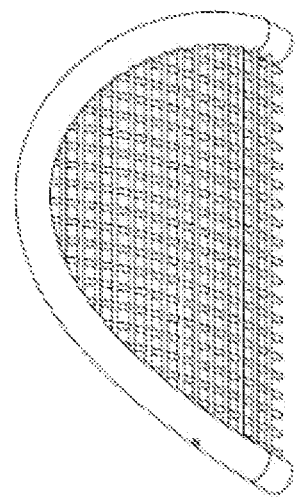
Figure 12A:
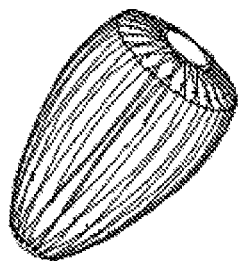
FIGS. 12A-12D are schematic structural view of an occluding woven net according to different embodiments.
Figure 12B:
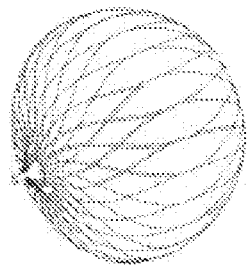
Figure 12C:
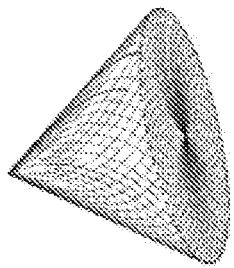
Figure 12D:
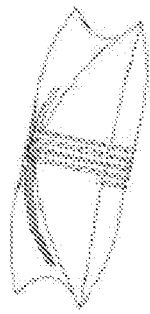

Further, referring to FIG. 11D, an inner expansion woven net 52 is provided at a concave place of the outer expansion frame 51 of each of the expandable arms 5. Two end portions of the outer expansion frame are connected to the lower clamp assemblies 2 and the connecting rod arms 6.

Further, a pore size of the inner expansion woven net 52 of each of the expandable arms 5 is less than an outer diameter of a regurgitation body.

The expandable arms 5 each are connected to the lower clamp assemblies 2 in a manner including but not limited to a spliced connection, a riveted connection, a welded connection or a threaded connection. The expandable arms 5 are made of an alloy having the shape memory function or a degradable polymer material.

For the expandable arms, the alloy includes but not limited to a nitinol and a magnesium alloy having the shape memory function, and the polymer material includes a degradable poly-L-lactic acid.

The clamp further includes the connecting rod arms 6, and each of the connecting rod arms 6 includes a connecting rod bottom plate 61 and connecting rod side plates 62 perpendicular to a side of the connecting rod bottom plate 61; a lower portion of each of the connecting rod side plates 62 is movably connected to the base body 31 of the base 3, and an upper portion of each of the connecting rod side plates 62 is movably connected to a linkage hole 26 of each of the lower clamp assemblies 2, thereby forming a four-rod linkage unit; and an accommodation groove formed by the connecting rod bottom plate 61 and the connecting rod side plates 62 is matched with an external contour of the lower portion of each of the lower clamp assemblies 2.

Each of the connecting rod arms 6 further includes a connecting rod hinge hole 63 in the lower portion of each of the connecting rod side plates 62; and a connecting rod linkage hole 64 is formed in the upper portion of each of the connecting rod side plates 62.

The lower portions of the two connecting rod side plates 62 are movably connected to two base connecting holes 33 of the base 3 through the connecting rod hinge hole 63, respectively, such as the hinged connection or the pivoted connection.

Likewise, an inner side of an upper edge of each of the connecting rod bottom plate 61 and the connecting rod side plates 62 of the connecting rod arm 6 is rounded or is provided with a turnup extending outward in an arc, to reduce the damage of the edge or the end portion to the tissue.

The occluding woven net 7 in the expanded state is of a hazelnut shape (FIG. 1, FIG. 7 and FIG. 12A), an ellipsoidal shape, a conical shape (FIG. 12C), an ingot shape, a pillow shape (FIG. 12D), a trumpet shape, a saddle shape, a spherical shape (FIG. 12B), an oblate spheroid shape or an irregular shape. A preserved hole for conveniently cooperating with a delivery system is formed in a top of the occluding woven net 7, for ease of delivery, release and separation of the delivery system. A bottom of the occluding woven net 7 is connected to a periphery of the locking unit 4 through end portions of the net, or connected to a top of the locking unit 4 through a bottom contracting end of the occluding woven net 7.

The connection herein includes any conceivable manner such as the welded connection and mechanical locking.

When not used or delivered, the occluding woven net 7 can be compressed to enter a smaller sheath; and after expanded, the occluding woven net can be set into various oblate or ellipsoidal shapes, provided that the expanded occluding woven net has the occluding effect.

The occluding woven net 7 is preferably woven by a shape memory metal and thermally treated into a specific shape. Substantially, the occluding woven net has the radial supporting force.

Therefore, the central occluding woven web achieves three functions: 1) it reduces the central regurgitation; 2) it decreases the stress on the leaflet during opening of the mitral valve; and 3) it effectively expands the orifice area.

Further, a biocompatible PET film is coated on an outer surface of each of the upper clamp assemblies 1, the lower clamp assemblies 2, the base 3, the locking unit 4, the expandable arms 5, the connecting rod arms 6 and the occluding woven net 7.

In another embodiment, at least part of each of the upper clamp assemblies 1, the lower clamp assemblies 2, the base 3, the locking unit 4, the expandable arms 5, the connecting rod arms 6 and the occluding woven net 7 is made of a biomaterial such as the polyester, silicon resin, stainless steel, cobalt alloy, nitinol, cobalt-chromium alloy or titanium alloy, and preferably the stainless steel or the cobalt-chromium alloy.

In another embodiment, the upper clamp assemblies 1, the lower clamp assemblies 2, the base 3, the locking unit 4, the expandable arms 5, the connecting rod arms 6 and the occluding woven net 7 each are made of a metal material or a metal alloy; and the metal material or the alloy is selected from a group consisting of common metals for implantation such as the stainless steel, cobalt alloy, cobalt-chromium alloy, titanium alloy or nitinol.

Finally, it should be noted that the above embodiments are merely intended to describe the technical solutions of the present invention, rather than to limit the present invention. Although the present invention is described in detail with reference to the above embodiments, those of ordinary skill in the art should understand that they may still make modifications to the technical solutions described in the above embodiments or make equivalent replacements to some or all technical features thereof, without departing from the essence of the technical solutions in the embodiments of the present invention.

What is claimed is:

1. A clamp, comprising upper clamp assemblies, lower clamp assemblies, a base, a locking unit and expandable arms, wherein
    the upper clamp assemblies and the lower clamp assemblies are quantitatively identical and cooperate in opening and closing to form a clamping portion;
    the base comprises a base body and a base support rod, and the base support rod is perpendicularly provided on an upper surface of the base body;
    the locking unit is movably sleeved on the base support rod, and a bottom of the locking unit abuts against and is supported on the upper surface of the base body;
    a lower portion of each of the upper clamp assemblies is fixedly provided on a side of the locking unit, and the lower clamp assemblies are movably connected to the locking unit and located below the upper clamp assemblies;
    each of the expandable arms is detachably provided on an upper portion of each of the lower clamp assemblies and extends toward two sides of a clamping bottom plate of each of the lower clamp assemblies, respectively;
    when the upper clamp assemblies and the lower clamp assemblies are in a working clamped state, an outer expansion edge of each of the expandable arms is located between two adjacent or opposite lower clamp assemblies to clamp valves on two sides of the clamping portion, thereby expanding a clamping range; and
    the expandable arms are deformable and are in a contracted state in delivery, wherein the clamp is compressed overall into a delivery system to reduce an injury in a procedure.

2. The clamp according to claim 1, wherein
    each of the upper clamp assemblies comprises elastic upper clamping plates having a shape memory function; at least one threading hole is formed in a plate body of each of the elastic upper clamping plates; and
    a side, facing toward each of the lower clamp assemblies, of each of the elastic upper clamping plate is provided with a rough structure, and the rough structure comprises a toothed structure, a barbed structure or a protrusive structure.

3. The clamp according to claim 2, wherein
each of the upper clamp assemblies further comprises an upper clamp connecting bottom plate;
two ends of the upper clamp connecting bottom plate are respectively provided with the elastic upper clamping plates;
the upper clamp connecting bottom plate and the elastic upper clamping plates at the two ends of the upper clamp connecting bottom plate are integrally formed into a concave structure;
an upper clamp through hole is formed in a middle of the upper clamp connecting bottom plate;
an upper clamp guiding limit hole is formed in a lower portion of each of the two elastic upper clamping plates in a penetrating manner, and the upper clamp guiding limit hole is configured to release a stress in an upper clamp heat treatment forming process; and
an upper surface of the upper clamp connecting bottom plate is attached to an underside of the locking unit, and an inner side of the lower portion of each of the two elastic upper clamping plates is attached to an outer side of the locking unit.

4. The clamp according to claim 2, wherein
each of the elastic upper clamping plates having the shape memory function has a preset expansion angle α, and α=30-135°.

5. The clamp according to claim 4, wherein
each of the lower clamp assemblies comprises a lower clamp bottom plate and lower clamp side plates perpendicularly provided on two sides of the lower clamp bottom plate, and the lower clamp bottom plate and the lower clamp side plates are formed into an accommodation cavity cooperating with each of the upper clamp assemblies; and
a lower portion of each of the lower clamp side plates is connected to an outward expansion plate and a hinge plate, and movably connected to the locking unit through the hinge plate expanding outward.

6. The clamp according to claim 5, wherein
a hinge hole for connecting each of the lower clamp assemblies to the locking unit is formed in the hinge plate in a penetrating manner; and
a linkage hole is formed in the outward expansion plate.

7. The clamp according to claim 6, wherein
the clamp further comprises a connecting rod arm, and the connecting rod arm comprises a connecting rod bottom plate and connecting rod side plates perpendicular to a side of the connecting rod bottom plate;
a lower portion of each of the connecting rod side plates is movably connected to the base body of the base, and an upper portion of each of the connecting rod side plates is movably connected to the linkage hole of each of the lower clamp assemblies, thereby forming a four-rod linkage unit; and
an accommodation groove formed by the connecting rod bottom plate and the connecting rod side plates is matched with an external contour of the lower portion of each of the lower clamp assemblies.

8. The clamp according to claim 5, wherein
an inner side of an upper edge of each of the lower clamp bottom plate and the lower clamp side plates is rounded or is provided with a turnup extending outward in an arc.

9. The clamp according to claim 4, wherein
the locking unit comprises a locking base;
a hollow locking accommodation cavity is formed in a lower portion of the locking base;
an oblique lug boss protruding toward the hollow locking accommodation cavity is provided on a sidewall of the hollow locking accommodation cavity; and
the oblique lug boss is configured to be embedded into the base support rod to locate the locking unit on the base.

10. The clamp according to claim 4, wherein
each of the expandable arms comprises a strip-shaped or tubular outer expansion frame, and each of the expandable arms comprises a semicircular shape, an ω shape formed by connecting two semi-rings, a semicircular shape formed by docking two irregular curves, a docked trapezoidal shape, or a U shape.

11. The clamp according to claim 10, wherein
an inner expansion woven net is provided at a concave place of the outer expansion frame of each of the expandable arms.

12. The clamp according to claim 11, wherein
a pore size of the inner expansion woven net of each of the expandable arms is less than an outer diameter of a regurgitation body.

13. The clamp according to claim 11, wherein
the expandable arms are respectively connected to the lower clamp assemblies in a manner comprising a spliced connection, a riveted connection, a welded connection or a threaded connection; and
the expandable arms are made of an alloy having the shape memory function or a degradable polymer material.

14. The clamp according to claim 13, wherein
the alloy comprises but is not limited to a nitinol and a magnesium alloy having the shape memory function, and the degradable polymer material comprises a degradable poly-L-lactic acid.

15. The clamp according to claim 4, wherein
each of the upper clamp assemblies comprises two elastic upper clamping plates oppositely arranged on two sides of the locking unit; and correspondingly, two lower clamp assemblies are provided.

16. The clamp according to claim 2, wherein
the rough structure is toothed rows or barbed rows obliquely formed from two sides of the plate body of each of the elastic upper clamping plates, or the rough structure is an integral toothed row structure continuously formed by the two sides of the plate body of each of the elastic upper clamping plates.

17. The clamp according to claim 2, wherein
the clamp comprises an occluding woven net;
the occluding woven net is located in a center of an upper portion of the clamp, and provided on the locking unit; and
the occluding woven net is linked with the expandable arms to change from a contracted state to an expanded state, thereby reducing central regurgitation, decreasing a stress on a leaflet, and preventing a damage to the leaflet.

18. The clamp according to claim 1, wherein
the clamp comprises an occluding woven net;
the occluding woven net is located in a center of an upper portion of the clamp, and provided on the locking unit; and
the occluding woven net is linked with the expandable arms to change from a contracted state to an expanded state, thereby reducing central regurgitation, decreasing a stress on a leaflet, and preventing a damage to the leaflet.

19. The clamp according to claim 18, wherein
the occluding woven net in the expanded state is of a hazelnut shape, an ellipsoidal shape, a conical shape, an ingot shape, a pillow shape, a trumpet shape, a saddle shape, a spherical shape, an oblate spheroid shape or an irregular shape;
a preserved hole for conveniently cooperating with the delivery system is formed in a top of the occluding woven net; and
a bottom of the occluding woven net is connected to a periphery of the locking unit through end portions of the net, or the bottom of the occluding woven net is connected to a top of the locking unit through a bottom contracting end of the occluding woven net.

20. The clamp according to claim 18, wherein
a biocompatible polyethylene terephthalate film is coated on an outer surface of each of the upper clamp assemblies, the lower clamp assemblies, the base, the locking unit, the expandable arms, the connecting rod arm and the occluding woven net.

\* \* \* \* \*